(12) United States Patent
Sulzbach et al.

(10) Patent No.: US 8,810,110 B2
(45) Date of Patent: Aug. 19, 2014

(54) MICRO-MECHANICAL COMPONENT WITH CANTILEVER INTEGRATED ELECTRICAL FUNCTIONAL ELEMENT

(75) Inventors: Thomas Sulzbach, Weisendorf (DE);
Wolfgang Engl, Erlangen (DE);
Christoph Richter, Forchheim (DE)

(73) Assignee: NanoWorld AG, Neuchatel (CH)

( * ) Notice: Subject to any disclaimer, the term of this patent is extended or adjusted under 35 U.S.C. 154(b) by 400 days.

(21) Appl. No.: 13/418,839

(22) Filed: Mar. 13, 2012

(65) Prior Publication Data
US 2012/0242189 A1 Sep. 27, 2012

(30) Foreign Application Priority Data
Mar. 24, 2011 (EP) .................................... 11401049

(51) Int. Cl.
| | |
|---|---|
| H01L 41/04 | (2006.01) |
| H02N 2/00 | (2006.01) |
| G01N 29/036 | (2006.01) |
| G01N 29/02 | (2006.01) |
| G01Q 10/04 | (2010.01) |
| G01Q 20/04 | (2010.01) |
| B81B 7/00 | (2006.01) |
| B82Y 35/00 | (2011.01) |

(52) U.S. Cl.
CPC ........ G01Q 20/04 (2013.01); G01N 2291/0427 (2013.01); B82Y 35/00 (2013.01); G01N 29/036 (2013.01); G01N 2291/0256 (2013.01); G01N 29/022 (2013.01); G01Q 10/045 (2013.01); B81B 7/0006 (2013.01)
USPC .......................................... 310/330; 310/331

(58) Field of Classification Search
CPC ...................................................... G01Q 20/04
USPC ................................................... 310/330–332
See application file for complete search history.

(56) References Cited

U.S. PATENT DOCUMENTS

| | | | | |
|---|---|---|---|---|
| 5,266,801 A | * | 11/1993 | Elings et al. .................... 850/40 |
| 5,354,985 A | * | 10/1994 | Quate ........................... 250/234 |
| 2006/0238206 A1 | | 10/2006 | Eng et al. | |
| 2009/0007645 A1 | | 1/2009 | Shih et al. | |
| 2011/0265227 A1 | * | 10/2011 | Shih et al. ........................ 850/33 |

FOREIGN PATENT DOCUMENTS

| | | | | |
|---|---|---|---|---|
| EP | 0 516 418 A1 | | 12/1992 | |
| JP | 2003302328 A | * | 10/2003 | ............. G01N 13/12 |
| WO | 2004/075204 A2 | | 9/2004 | |

OTHER PUBLICATIONS

European Search Report for corresponding European Application No. EP 11 40 1049 Issued Jun. 24, 2011.

* cited by examiner

*Primary Examiner* — J. San Martin
(74) *Attorney, Agent, or Firm* — Renner, Otto, Boisselle & Sklar, LLP

(57) ABSTRACT

A micro-mechanical component including a support element and a cantilever with integrated electrical functional element to which at least two electrical supply lines implemented as printed conductors on the cantilever are routed. The invention proposes to arrange at least one each of the supply lines on the two opposite flat surfaces of the cantilever and/or the support element. The functional element is supplied by the first supply line on a first flat surface, with the second supply line on the opposite flat surface serving as return line.

14 Claims, 4 Drawing Sheets

MICRO-MECHANICAL COMPONENT WITH CANTILEVER INTEGRATED ELECTRICAL FUNCTIONAL ELEMENT

CROSS-REFERENCE TO RELATED APPLICATION

The present application claims priority under 35 USC §119 to European Patent Application No. 11 401 049.9 filed Mar. 24, 2011, the entire disclosure of which is incorporated herein by reference.

TECHNICAL FIELD OF THE INVENTION

The invention relates to a micro-mechanical component having a support element and at least one cantilever, with at least one electrical functional element that is integrated in the cantilever and arranged on a first flat surface of the cantilever, and with at least two electrical supply lines for the functional element that are implemented as printed conductors on the cantilever.

DESCRIPTION OF THE RELATED ART

Micro-mechanical components are used, for example, in scanning probe microscopy (SPM). SPM has become established as a surface analysis technology that permits, among other things, the imaging of surface topographies with a resolution of a few nanometers or even down into the nuclear range. An essential core element of this technology is the scanning probe that contains a micro-mechanical cantilever with an integrated scanning tip. The nature and the quality of the probes contribute essentially to the achievable resolution of the surface analysis. For producing the probes, different processes have become established that are based either on the etching of mono-crystalline silicon or on thin layers, preferably made of silicon nitride.

A significant disadvantage of scanning probe microscopy as such is the slow speed of the analysis because the probe scans the surface in a point-by-point grid pattern. The speed of the grid scan is limited by the grid pattern mechanism, on the one hand, but also by the resonant frequency of the cantilever of the probe. Current developments in the field of scanning probe microscopy address this problem by developing new systems and probes that operate at a distinctly higher speed.

In order to achieve the necessary increase of the resonant frequency of the probes for such fast scanning probe microscopes without simultaneously changing the rigidity of the cantilever, all dimensions of the cantilever need to be significantly reduced. Typically, the length of these high-frequency cantilevers is less than 20 µm, their width less than 5 µm, and their thickness significantly less than 1 µm, and therefore, at least as far as length and thickness are concerned, smaller by a factor of approximately 10 than the cantilevers of SPM probes in common use at this time.

These dimensions of the cantilever pose significantly higher demands on the scanning probe microscope. Commonly, the deflection of the cantilever is realized via the so-called light pointer principle where a laser beam is focused on the back side, i.e. the side facing away from the test sample. The movement of the reflected laser beam due to the bending of the micro-mechanical cantilever is measured at a distance of commonly several centimeters by means of a segment photo diode. This makes it possible to detect a vertical cantilever movement due to bending with a resolution that is distinctly better than 1 µm.

In the case of the smaller high-frequency cantilevers with reduced dimensions, the laser beam must be focused on a diameter that is reduced commensurate with the cantilever size. Especially with the commonly preferred arrangement of a SPM probe moving in a grid pattern above a test sample in fixed position, it is quite difficult to achieve a focus diameter of only a few millimeters. In such an arrangement, the focal point must be moved along with the SPM probe. This requires at least one optical component, usually a lens, to be guided along. However, on the one hand, this optical element needs to have a high optical aperture in order to achieve a sufficiently small focal diameter, while on the other hand also having a low mass, so that it can be moved fast enough.

As a non-optical method for the detection of the deflection of micro-mechanical cantilevers, the integration of a piezoresistive strain sensor has become established.

For this purpose, a local inversion of the doping is created in the surface of a silicon cantilever that is semi-insulating in relation to the actual cantilever material. Via suitable supply lines, a constant current is applied, and the piezoresistive change of the resistance due to the extension of the cantilever surface during the deflection of the cantilever is measured by means of the change of the voltage.

However, the scaling of this concept for smaller dimensions is often restricted due to the existing structuring processes. With the inexpensive and widely used contact lithography, it is possible to typically achieve minimal structure dimensions of 1.5 to 2 µm. As a consequence, the cantilever into which the strain sensor is to be integrated needs to be correspondingly larger. For the line in and the line out as well as the necessary minimum distance between the lines and the edge of the cantilever, 7.5 to 10 µm are required, i.e. approximately 5 times the minimum structure width. It is possible to achieve somewhat smaller dimensions if the structuring of the strain sensor is done along with the structuring of the cantilever itself which will then have to be U or V-shaped. However, even in this case, the minimum width is approximately 6 µm if the contact lithography process is used. The cantilever geometry is therefore limited significantly above that which can be made with the same lithography processes.

Another disadvantage of known probes with integrated piezoresistive strain sensors is their costly integration in the scanning probe microscope. Instead of the usual spring clamping of passive SPM probes, probes with piezoresistive strain sensors require electrical contacting of the probes. For this purpose, they are commonly glued to a small circuit board and connected to it by means of bonded wires. The assembly procedures required for this make these probes considerably more expensive. In addition, a costly modification of the SPM scanning head is required in order to be able to install the assembled probes.

Similar problems are encountered with probes using other integrated sensors, as for example temperature sensors in the form of thermal contact sensors, thermo-resistors. Here, too, the electrical supply lines require a significant modification of the scanning head.

Based on the prior art described above, the invention addresses the problem of proposing a method for significantly reducing the width of the cantilever of such a micro-mechanical component, thereby making it suitable for higher frequencies.

SUMMARY OF THE INVENTION

According to the invention, this problem is solved by a micro-mechanical component as described herein.

The micro-mechanical component according to the invention includes a support element and at least one cantilever, with at least one electrical functional element that is integrated in the cantilever and arranged on a first flat surface of the cantilever, and with at least two electrical supply lines for the functional element. At least one first supply line is arranged on the first flat surface and at least one second supply line is arranged on a second flat surface of the cantilever that is located opposite the first flat surface. The second supply line extends on the first flat surface up to the functional element, with the second supply line having a local electrical connection between the first and the second flat surface of the cantilever.

Preferably, the local electrical connection is via a narrow side of the cantilever and/or via a local opening in the cantilever, that is preferably realized as a local printed circuit. In case of a connection established via a local opening, the local opening may be lined and/or completely or partially filled with electrically conductive material. In a preferred embodiment of the invention, the supply lines on the two flat surfaces consist of materials of different electrical conductivity that are in contact at the local electrical connection.

In one embodiment of the micro-mechanical component according to the invention, the cantilever has a scanning tip at its free end that is preferably arranged at that flat surface of the cantilever that faces away from the support element, with the local opening formed at the scanning tip and preferably at the apex of the scanning tip. Preferably, the electrical functional element is also arranged at that flat surface of the cantilever that is facing away from the support element. In one variant of the invention, the cantilever consists of a semiconductor material. In this case, the local electrical connection from the first flat surface to the second flat surface is achieved by a local inversion of the doping of the cantilever material. In addition, the electrical supply lines for the electrical functional element may extend not only on different flat surfaces of the cantilever but may continue on different flat surfaces of the support element.

In the proposed micro-mechanical component, the cantilever may have a length of less than 500 µm, a width of less than 50 µm, and a thickness of less than 10 µm; a length of less than 50 µm, a width of less than 5 µm, and a thickness of less than 1 µm; or a length of less than 10 µm, a width of less than 3 µm, and a thickness of less than 0.5 µm.

As integrated functional element for the proposed micro-mechanical component, a piezoresistive strain sensor, an actuator for bending the cantilever, a piezoelectric converter, a thermosensor, a photo detector, a magnetic resistance sensor, or a gas sensor may be used as functional element. Here, the micro-mechanical component can be used specifically as an SPM probe. In principle, according to the invention, the examples of integrated electrical functional elements referred to above may also be combined. The integration of actuator and sensor in the cantilever makes an independent microsystem possible that permits the parallelization of the scanning with the cantilever without restriction.

Below, the invention is explained once again in detail with reference to several embodiments shown schematically in the drawing. Additional characteristics of the invention are given in the following description of the embodiment of the invention in conjunction with the claims and the attached drawing. The individual characteristics of the invention may be realized either individually by themselves or in combinations of several in different embodiments of the invention.

DETAILED DESCRIPTION OF THE INVENTION

Figure 1:
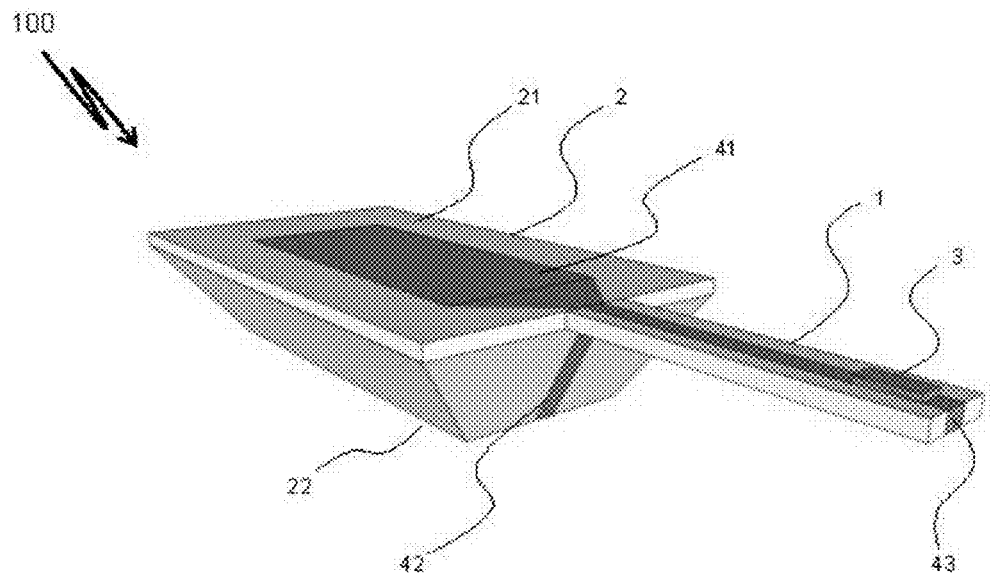
FIG. 1 shows a perspective view of a first micro-mechanical component according to the invention without scanning tip and a local electrical connection, formed at the edge, between the flat surfaces of the cantilever.

The FIGS. 1 to 7 each show a micro-mechanical component 100 according to the invention with a micro-mechanical cantilever 1 that is attached to a support element 2 and comprises at least one integrated electrical functional element 3. According to the invention, at least one supply line 41 to the functional element 3 integrated in the micro-mechanical cantilever 1 is provided via a first flat surface 21 of the support element 2 to which the cantilever 1 is attached and via the corresponding first flat surface 21 of the cantilever 1, and at least one additional second supply line 42 (return line) is provided via the opposite second flat surface 22 of the support element 2 and of the cantilever 1. The electrical functional element 3 is arranged on the flat surface 21 of the cantilever 1 that is facing away from the support element 2. At least in the special case of two supply lines 41, 42, this makes it possible for the micro-mechanical component 100 to be electrically contacted from the two opposing sides of the support element 2 by means of mechanical contacts that are simple to realize.

In addition, a significant reduction of the dimensions of the micro-mechanical cantilever 1 with integrated electrical functional element 3 is possible because the supply line and the return line do not have to be integrated on the same flat surface 21 or 22 of the cantilever 1 but on surfaces that are opposite the flat surfaces 21, 22 of the cantilever 1. This permits the size of the cantilever 1 to be reduced at least by a factor of 2.

Figure 5:
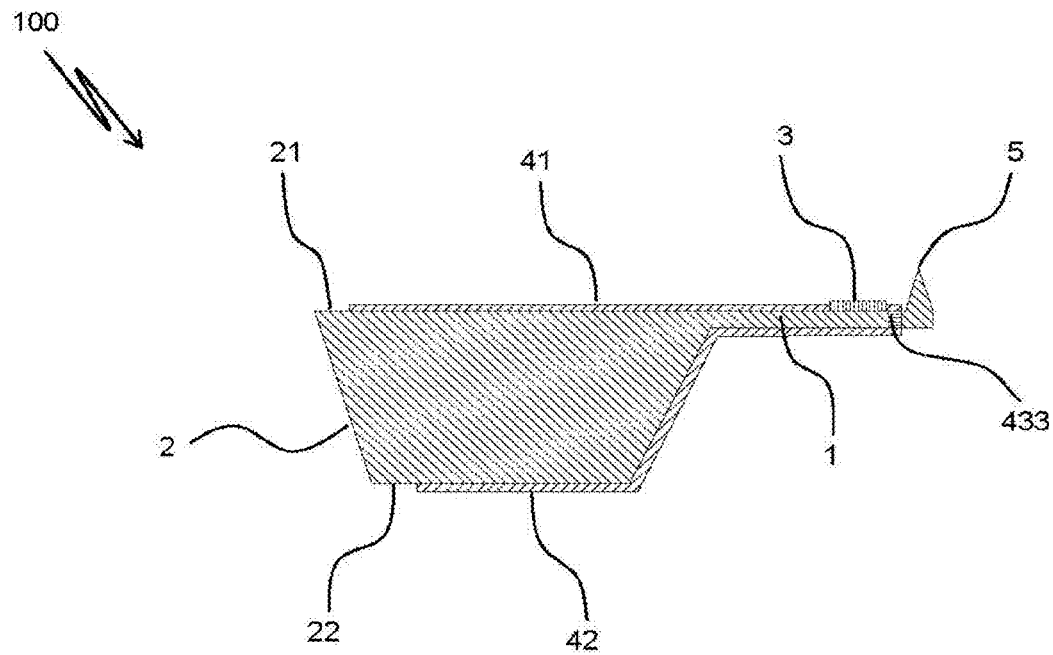
FIG. 5 shows a longitudinal section view of a fourth micro-mechanical component according to the invention, as a variant of the micro-mechanical component in FIG. 4.

A local electrical connection between one or several supply lines 41 (incoming line) on one flat surface 21 of the support element 2 and of the cantilever 1 and one or several supply lines 42 (return lines) on the opposite flat surface 22 is provided according to the invention by one or several local vertical electrical connections 43, 431, 432, 433. In the embodiments shown in FIGS. 1, 2, these are provided in the form of printed conductors 43, 432 across the edge and the narrow side of the cantilever 1, and in the embodiments shown in the FIGS. 3, 4, 5, 6 as through-contacts 431, 433 in the cantilever 1. The through-contacts 431, 433 can be implemented as openings 431 (FIG. 3, 4) that are etched through the cantilever 1 and are equipped with conductive material, or by means of local dopings 433 through the cantilever 1 (FIG. 5, 6). In the embodiments shown in FIGS. 4-7, the scanning tip 5 is arranged at the flat surface 21 of the cantilever 1 that faces away from the support element 2.

Figure 6:
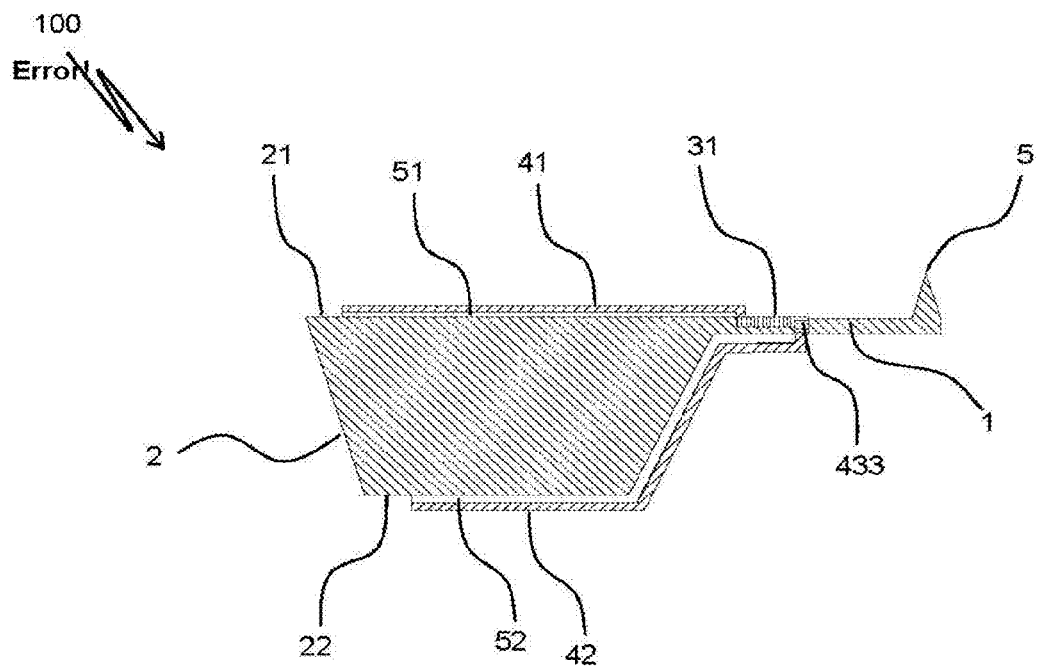
FIG. 6 shows a longitudinal section view of a fifth micro-mechanical component according to the invention that is similar to the micro-mechanical component in FIG. 5, with a functional element that is arranged at a different location of the cantilever.

The embodiment of the invention shown in FIG. 6 shows an SPM probe 100 with integrated piezoresistive deflection detection. The functional element 3 that is integrated in the cantilever 1 is a piezoresistive resistor 31 that converts the elongation of the cantilever surface, and therefore its deflection, to an electric signal. According to the invention, the supply line 41 is routed via the flat surface 21 of the SPM probe 100 in whose surface the piezoresistive resistor 31 is realized. Insulating layers 51 and 52, respectively, are arranged between the supply line 41 on the flat surface 21 and also between the supply line 42 on the flat surface 22 and the support element 2 or the cantilever 1. The feed-through 43 to the back side of the cantilever can be created by local inversion by means of doping. A low-resistance connection 433 to the back side of the cantilever 1 can be created with a sufficiently high doping concentration and depth. At the same time, via such a region doped with high concentration, it is possible to provide an electrical contact between the usually highly resistive, weakly doped piezoresistive resistor 31 and a metallic printed conductor 42 that is located on the opposite side according to the invention. The scanning tip 5 that is necessary for the SPM probe 100 can be etched either in advance, or can be grown later by means of electron-beam-induced deposit. The insulating layers 51, 52 are not limited to the embodiment shown in FIG. 6.

This configuration makes it possible to limit the dimensions of the cantilever 1 with integrated deflection detection to a few micrometers of length and width and some hundreds of nanometers of thickness so that resonant frequencies of more than 10 MHz can be achieved with a spring stiffness of approximately 40 N/m that is common for a dynamic AFM. However, with an altered cantilever geometry, resonant frequencies of distinctly larger than 1 MHz at a spring stiffness of 0.2 N/m are also possible, as needed for contact mode AFM measurements at high speed. With supply lines integrated on one side of the probe, as in prior art, only distinctly lower resonant frequencies are possible due to the larger minimum cantilever dimensions at the same spring stiffness.

Figure 7:
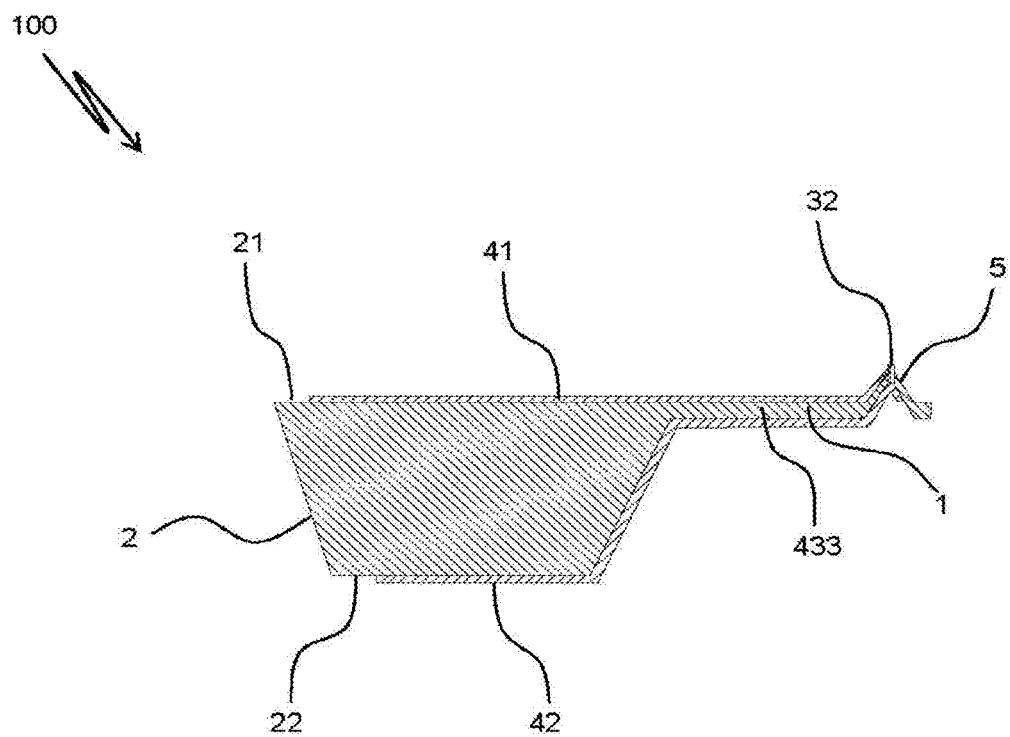
FIG. 7 shows a longitudinal section view of a sixth micro-mechanical component according to the invention where the local electrical connection is arranged at the apex of the scanning tip.

As another embodiment of the invention, FIG. 7 shows an SPM probe 100 with integrated thermo-contact temperature sensor 32. This probe 100 consists of a micro-mechanical cantilever 1 with a shaped scanning tip 5. At the apex of the scanning tip 5, there is a passage that can be created by means of lithography or etching, for example, or by means of erosion with focused ion beams. The two opposite flat surfaces 21, 22 of the probe 100 and therefore also of the cantilever 1 are coated with different metals as supply lines 41, 42 that can be applied by means of electron beam evaporation, for example. Via the opening in the scanning tip 5, the two metals are connected locally with each other, forming a thermo-contact 32. Preferably, pairs of metals with a high Seebeck coefficient are used that ensure optimum thermal sensitivity. In order to avoid parasitic short-circuits over the probe or cantilever edges, one or both metal coatings may also be lithographically structured. An additional functional element (not shown) can be arranged on the flat surface (21) facing away from the support element (2). The probes according to the invention can also be contacted with an only slightly modified probe holder, as described above, and do not require a carrier mounted in a fixed position.

Going beyond this example, it is also possible to integrate other functional elements like local field emitters, GMR sensors, or photo diodes in the scanning tip 5 of the SPM probes 100.

Instead of the deflection sensor 31, it is also possible to integrate an electro-mechanical actuator 3 in the cantilever 1 and to contact it according to the invention from two opposite flat surfaces 21, 22 of the component. Piezoelectric systems of PZT, ZnO, or AlN layers, for example, may serve as actuator elements. In principle, however, these piezoelectric systems can also be used in reverse for transforming mechanical energy to electric energy. Such a use is explicitly included.

Another embodiment of the invention is a combination of electrical and mechanical gas sensors. According to the invention, polymer and solid-state based gas sensors are easier to integrate in micro-mechanical cantilevers 3. This makes it possible to perform a combination of direct electric measurement and characterization via a change of the mechanical properties of the cantilever (bending due to induced surface tensions, change of the resonant frequency due to changes in mass, etc.).

Figure 2:
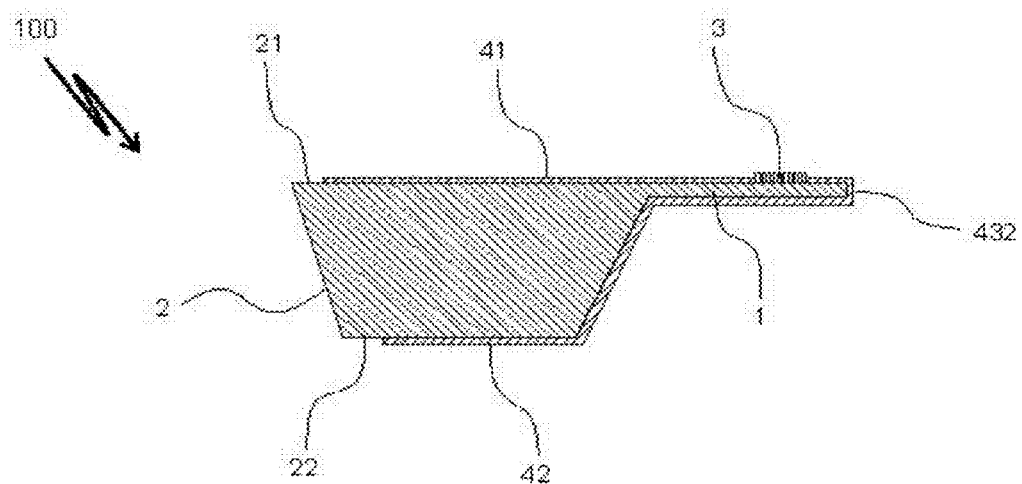
FIG. 2 shows a longitudinal section view of the micro-mechanical component from FIG. 1.
Figure 3:
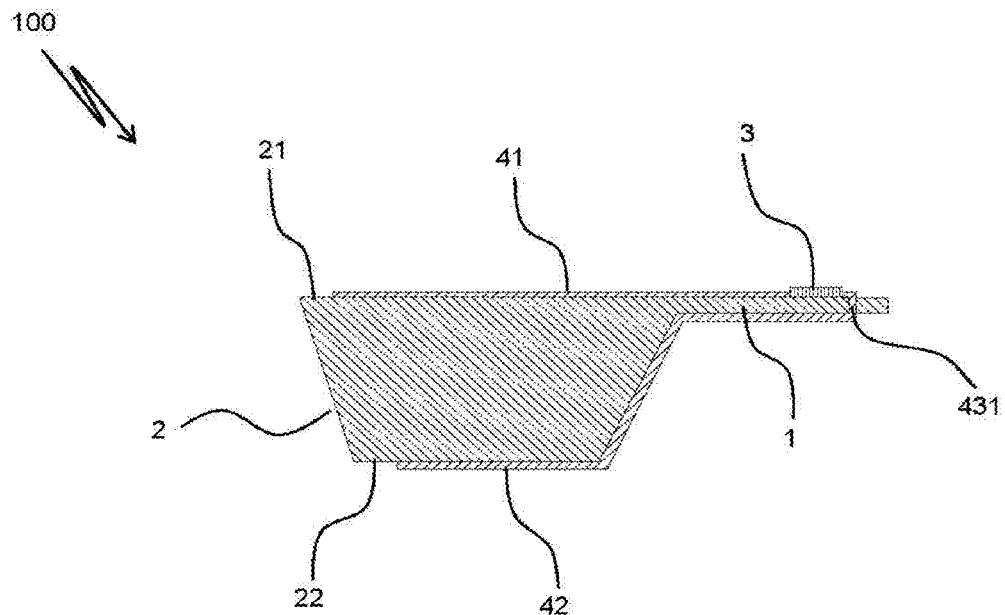
FIG. 3 shows a longitudinal section view of a second micro-mechanical component according to the invention without scanning tip and with a local electrical connection between the flat surfaces of the cantilever realized inside the cantilever.
Figure 4:
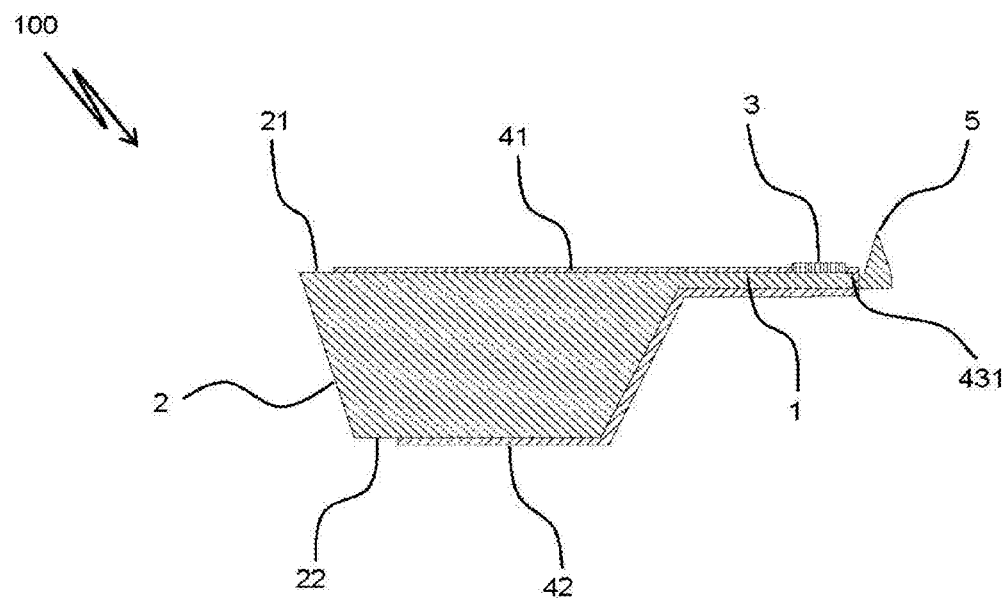
FIG. 4 shows a longitudinal section view of a third micro-mechanical component according to the invention that is similar to the micro-mechanical component in FIG. 3, but with a scanning tip.
Figure 8:
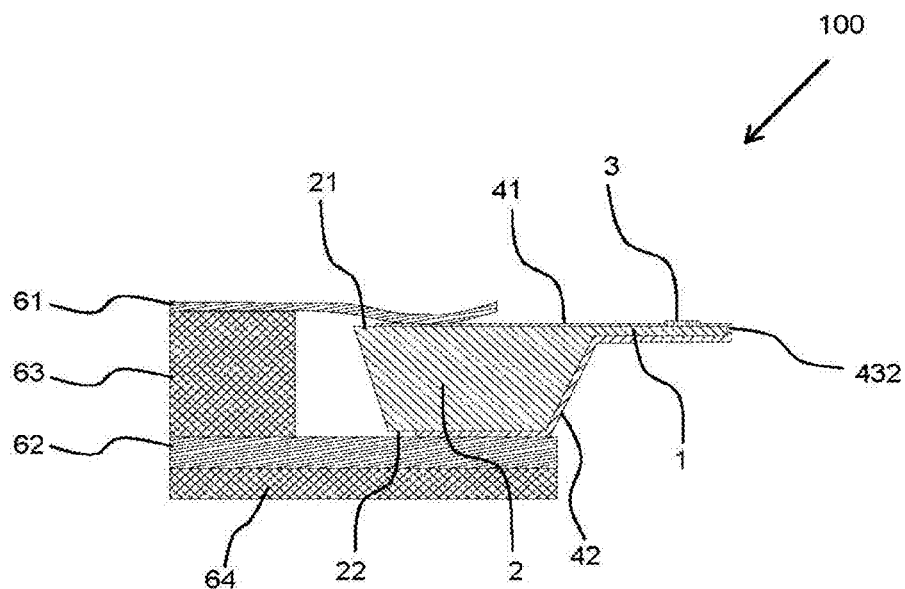
FIG. 8 shows a longitudinal section view of the micro-mechanical component in FIG. 2, connected with a SPM scanning head.

FIG. 8 shows the SPM probe 100 of the FIGS. 1, 2 mounted on an SPM scanning head of which only the attachment device for the probe 100 is shown. In all embodiments of the invention, contacting can be accomplished in the same way. The electrical contacting of the SPM probe 100 with integrated piezoresistive strain sensor 31 in the SPM scanning head can be performed via the spring contacts 61 and 62 that are electrically insulated from each other and the rest of the setup by means of the insulators 63 and 64. This only requires a slight modification of the usual configuration of the probe holder in the SPM scanning head. According to the prior art, in a common design feature the probe 100 is pressed against a metallic carrier by a metallic spring. The supply and return line can be contacted via these two elements of the probe holder. The only thing needed is an electrical connection between the spring on the one side and the carrier on the other side with the electronic control system of the SPM system. Such a modification is easy to implement. A permanent connection of the SPM probe with a carrier, and the high assembly costs for the consumable probe that this connection would involve, are not necessary, resulting in a significant cost reduction for the user.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. A micro-mechanical component including a support element and at least one cantilever, with at least one electrical functional element that is integrated in the cantilever and arranged on a first flat surface of the cantilever, and with at least two electrical supply lines for the functional element that are implemented as printed conductors on the cantilever, wherein at least one first supply line is arranged on the first flat surface and at least one second supply line is arranged on a second flat surface of the cantilever that is located opposite the first flat surface, extending on the first flat surface up to the functional element, with the second supply line having a local electrical connection between the first and the second flat surface.

2. The micro-mechanical component according to claim 1, wherein the local electrical connection is realized via a narrow side of the cantilever and/or a local opening in the cantilever.

3. The micro-mechanical component according to claim 2, wherein the local electrical connection is a local printed conductor.

4. The micro-mechanical component according to claim 2 wherein the local opening is at least partially filled with electrically conductive material.

5. The micro-mechanical component according to claim 1, wherein the supply lines on the two flat surfaces consist of different conductive materials that are in contact at the local electrical connection.

6. The micro-mechanical component according to claim 1, wherein the cantilever comprises at its free end a scanning tip that is arranged at the flat surface of the cantilever that faces away from the support element.

7. The micro-mechanical component according to claim 6, wherein the local opening at the scanning tip is formed preferably in the apex of the scanning tip.

8. The micro-mechanical component according to claim 1, wherein the electrical functional element is arranged at the flat surface of the cantilever that faces away from the support element.

9. The micro-mechanical component according to claim 1, wherein the cantilever consists of a semiconductor material.

10. The micro-mechanical component according to claim 1, wherein the local electrical connection from the first flat surface to the second flat surface is realized by a local inversion of the doping of the cantilever material.

11. The micro-mechanical component according to claim 1, wherein the electrical supply lines to the functional element extend on different flat surfaces of the cantilever and the support element.

12. The micro-mechanical component according to claim 1, wherein the cantilever has a length of less than 500 µm, a width of less than 50 µm, and a thickness of less than 10 µm or a length of less than 50 µm, a width of less than 5 µm, and a thickness of less than 1 µm or a length of less than 10 µm, a width of less than 3 µm, and a thickness of less than 0.5 µm.

13. The micro-mechanical component according to claim 1, wherein the integrated functional element is a piezoresistive strain sensor, an actuator for bending the cantilever, a piezoelectric converter, a thermo-sensor, a photo detector, a magnetic resistance sensor, or a gas sensor.

14. The micro-mechanical component according to claim 1, wherein the micro-mechanical component (100) is a SPM probe.

\* \* \* \* \*